(12) United States Patent
Jackson

(10) Patent No.: US 8,841,823 B2
(45) Date of Patent: Sep. 23, 2014

(54) ULTRASONIC TRANSDUCER WEAR CAP

(75) Inventor: Todd Jackson, Walworth, NY (US)

(73) Assignee: Ascent Ventures, LLC, Pittsford, NY (US)

( * ) Notice: Subject to any disclaimer, the term of this patent is extended or adjusted under 35 U.S.C. 154(b) by 480 days.

(21) Appl. No.: 13/242,025

(22) Filed: Sep. 23, 2011

(65) Prior Publication Data

US 2013/0074602 A1    Mar. 28, 2013

(51) Int. Cl.
*H01L 41/053* (2006.01)
*G01N 29/24* (2006.01)
*G01N 29/28* (2006.01)

(52) U.S. Cl.
CPC ............... *G01N 29/24* (2013.01); *G01N 29/28* (2013.01)
USPC ........... 310/340; 310/311; 310/326; 310/336; 310/345

(58) Field of Classification Search
USPC ......... 310/311, 326, 327, 335–337, 348, 340, 310/345
See application file for complete search history.

(56) References Cited

U.S. PATENT DOCUMENTS

| | | | |
|---|---|---|---|
| 3,109,155 A | 10/1963 | Degen | |
| 3,230,402 A * | 1/1966 | Nightingale et al. | 310/338 |
| 3,360,665 A * | 12/1967 | Boswell | 310/328 |
| 3,890,423 A * | 6/1975 | Zacharias, Jr. | 310/335 |
| 4,211,949 A | 7/1980 | Brisken et al. | |
| 4,387,720 A | 6/1983 | Miller | |
| 4,600,228 A | 7/1986 | Tarbuck | |
| 4,852,416 A | 8/1989 | Boone et al. | |
| 5,050,436 A | 9/1991 | Kunii et al. | |
| 5,083,550 A * | 1/1992 | Krauss et al. | 601/4 |
| 5,576,492 A | 11/1996 | Phalin | |
| 5,737,963 A | 4/1998 | Eckert et al. | |
| 5,959,211 A | 9/1999 | Wagner et al. | |
| 6,072,312 A | 6/2000 | Van Den Berg | |
| 6,626,834 B2 | 9/2003 | Dunne et al. | |
| 6,800,987 B2 | 10/2004 | Toda | |
| 6,998,761 B1 * | 2/2006 | Frank et al. | 310/328 |
| 7,157,058 B2 * | 1/2007 | Marhasin et al. | 422/128 |
| 7,392,720 B2 | 7/2008 | Howarth et al. | |
| 7,552,634 B2 | 6/2009 | Huber et al. | |
| 7,591,182 B2 | 9/2009 | Sato et al. | |
| 8,102,734 B2 | 1/2012 | Sliwa et al. | |
| 8,191,422 B2 | 6/2012 | Maruyama et al. | |
| 8,196,471 B2 | 6/2012 | Han et al. | |
| 8,381,591 B2 | 2/2013 | Maev et al. | |
| 2003/0065263 A1 * | 4/2003 | Hare et al. | 600/439 |
| 2003/0171700 A1 * | 9/2003 | Martin et al. | 601/2 |
| 2004/0000838 A1 | 1/2004 | Toda | |
| 2007/0062290 A1 | 3/2007 | Roh et al. | |
| 2007/0093702 A1 * | 4/2007 | Yu et al. | 600/326 |
| 2009/0288490 A1 | 11/2009 | Maruyama et al. | |
| 2010/0199952 A1 * | 8/2010 | Schlegl | 123/472 |
| 2011/0114303 A1 * | 5/2011 | Rhim | 165/185 |
| 2012/0223618 A1 * | 9/2012 | Clark et al. | 310/322 |

\* cited by examiner

*Primary Examiner* — Thomas Dougherty
(74) *Attorney, Agent, or Firm* — Brown & Michaels, PC

(57) ABSTRACT

A wear cap including a flexible barrel and a rigid disc enables a high-frequency ultrasonic transducer to properly align to the surface of a material to be tested. The wear cap may be employed for any type of contact sensor that requires a protective wear cap and that needs to align to the surface of a material to be tested. An ultrasonic transducer assembly includes a wear cap and an ultrasonic transducer. The ultrasonic transducer is mounted in the wear cap and includes a transducer body with a cylindrical shape. A method of producing a wear cap for an ultrasonic transducer includes selecting a flexible material, forming a flexible barrel from the flexible material, selecting a rigid material, forming a rigid disc from the rigid material, and affixing the rigid disc to an end of the flexible barrel.

19 Claims, 5 Drawing Sheets

PRIOR ART

ULTRASONIC TRANSDUCER WEAR CAP

REFERENCE TO RELATED APPLICATIONS

The subject matter of this application is related to the subject matter in a co-pending application entitled "APPARATUS FOR ULTRASONIC TRANSDUCER OR OTHER CONTACT SENSOR PLACEMENT AGAINST A TEST MATERIAL", filed on the same day as the present application. The aforementioned application is hereby incorporated herein by reference.

BACKGROUND OF THE INVENTION

1. Field of the Invention

The invention pertains to the field of ultrasonic transducers. More particularly, the invention pertains to wear caps for ultrasonic transducers.

2. Description of Related Art

Wear caps with rigid barrels for low-frequency ultrasonic transducers are standardly used in the ultrasonic test and measurement industry. FIG. 1 shows a prior art ultrasonic transducer design with a generally cylindrical body 10, a front surface 12 on the bottom of the cylindrical body 10, and an electrical connector 14 extending from the side of the body 10. For low-frequency transducers, the purpose of a replaceable wear cap is to serve as a low-cost mechanism to protect the active end of the transducer against damage. The wear cap is then replaced when it becomes worn or damaged. Other such wear caps are typically integrated into the design of the transducer body, including designs currently on the market from Olympus NDT Inc. (Waltham, Mass., US) and GE Energy Services (Atlanta, Ga., US).

As shown in FIG. 2 and FIG. 3, a wear cap includes a protective layer 22 that is affixed to the front surface 12 of a transducer and which protects the front transducer surface 12 against damage. The wear cap may include a rigid barrel 20 that slips around the transducer body 10 to hold the protective layer 22 against the front transducer surface 12. An o-ring 26 mounted in the rigid barrel 20 may be used to grip the transducer body 10 and secure the transducer in the wear cap. The rigid barrel 20 of the wear cap may include a notch 24 to receive the electrical connector 14 of the ultrasonic transducer.

To ensure that the stimulus wave generated by an ultrasonic transducer is conducted to the test material and that reflected waves are conducted back to the transducer, the transducer must make good physical contact with the inside surface of the wear cap and the wear cap outside surface must contact the test surface 30 as shown in FIG. 4. In addition, the transducer should be placed perpendicularly to the surface such that the ultrasonic beam 40 is reflected back to the transducer from the test surface. Any misalignment of the transducer in the wear cap causes the ultrasonic beam 50 to be misdirected, as shown in FIG. 5.

U.S. Pat. No. 3,109,155, entitled "PROTECTIVE CASING FOR AN ULTRASONIC TRANSDUCER" and issued Oct. 29, 1963 to Degen, discloses a protective deflector casing for electro-ultrasonic transducers, particularly a single transducer for detection of passing vehicles.

U.S. Pat. No. 4,211,949, entitled "WEAR PLATE FOR PIEZOELECTRIC ULTRASONIC TRANSDUCER ARRAYS" and issued Jul. 8, 1980 to Brisken et al., discloses a linear transducer array for 90-degree or other wide angle sector scans. The transducer array is covered by a body-contacting wear plate made of a material such as filled silicone rubber or polyurethane epoxy in which the longitudinal sound velocity is equal to or less than that in the body and in which the acoustic impedance for longitudinal sound waves is approximately equal to that of the body. Refraction, if it occurs, enhances the field of view without reducing the transmission of acoustic energy. The wear plate provides mechanical support for a fragile front surface matched array.

U.S. Pat. No. 6,072,312, entitled "ENCAPSULATED TRANSDUCER HAVING A PROTECTIVE SLEEVE" and issued Jun. 6, 2000 to Van Den Berg, discloses an encapsulated transducer. The injection-molded encapsulation is a monolith of cured moldable material ensconcing a sensing element proximate the front end and a portion of an information-transmitting medium emanating from the back end. A component alignment pre-form operatively couples the sensing element with the information-transmitting medium. The component alignment pre-form includes a front ferrule and a rear ferrule bonded thereto and linearly spaced apart along a long axis. The component alignment pre-form further includes an annular recess in which the sensing element or coil is placed so that it is linearly spaced and aligned along the common long axis in which the front and rear ferrules are aligned. A first lead of the coil is electrically connected to the front ferrule and a second lead of the coil is electrically connected to the rear ferrule. A back end of the component alignment pre-form receives a stripped end of the cable such that a center conductor mates with the front ferrule and a coaxial conductor mates with the rear ferrule. The conductors are electrically and mechanically connected to the front and rear ferrules. A protective sleeve is then fitted over the coil thereby forming a sleeved coil and cable assembly. This sleeved coil and cable assembly is encapsulated by an injection molding process which provides the durable encapsulation which bonds with itself and with the sleeved coil and cable assembly. The sleeved coil and cable assembly is symmetrically disposed within the encapsulation and the encapsulation includes an integrally formed protective wall having a uniform thickness along a forwardmost portion of the sensing element.

U.S. Pat. No. 6,800,987, entitled "PROTECTIVE HOUSING FOR ULTRASONIC TRANSDUCER APPARATUS" and issued Oct. 5, 2004 to Toda, discloses a protective cover or grid for an ultrasound transducer. The cover includes a series of vertically-spaced members separated from one another by a pre-determined distance. Each member is of uniform width and arranged in a cylindrical shape. The protection grid includes a cavity for a cylindrical transducer. The protection grid operates as both a physical protection mechanism for protecting the housed cylindrical transducer as well as operating as an impedance matching device.

Such wear caps are offered only for low-frequency transducers, typically 5-MHz or lower, although Olympus currently provides a single offering for a 10-MHz transducer. Low-frequency transducers are tolerant of wear caps, because low-frequency ultrasound passes through the wear cap material easily. The basic design of a wear cap is a layer of material that is held against the transducer front face. In some implementations, an assembly of either metal or plastic is used to hold the wear cap layer rigidly against the transducer front surface. In other implementations, a wear cap may have the shape of a cup formed as a wear cap layer affixed to a rigid barrel, and the transducer slides into the barrel until it makes contact with the wear cap layer.

Wear caps are traditionally not offered for high-frequency transducers for several reasons, namely:

1. High-frequency ultrasound attenuates rapidly in most materials and can be strongly attenuated by passing through a wear cap.

2. High-frequency ultrasound is reflected very strongly at boundaries between materials, so the addition of a wear cap layer may cause ultrasound to be reflected by the wear cap rather than transmitted to the test material through the wear cap. In fact, if there is any airspace between the transducer's front face and the inside of the wear cap, the high-frequency ultrasound is completely reflected back to the transducer. Ultrasonic measurements are therefore not possible if the inside surface of the wear cap and the front surface of the transducer do not make good contact.

3. High-frequency ultrasound is highly directional. In a pulse-echo type of ultrasonic test application, the ultrasonic beam emitted by a high-frequency transducer must reach and be reflected by a test material surface and must then return to the transducer, hence the name pulse-echo. The addition of a wear cap between the high-frequency transducer and the test material surface may misalign the transducer relative to the test material surface, causing the reflected ultrasonic beam to miss the transducer and therefore not be detected by the transducer.

Because of the above performance issues, wear caps are not conventionally offered for use with high-frequency ultrasonic transducers. Pulse/echo layer thickness (PELT) gauges utilize high-frequency ultrasonic contact transducers, and there is a need to protect the face of these transducers against physical damage, and also a need to employ an intermediate material layer between the transducers and the test material surface so as to enable thickness measurements to be performed more readily. Rigid plastic wear caps for use with PELT gauge high-frequency ultrasonic transducers have been on the market since the 1990s, but there are many performance degradation issues related to these rigid wear caps.

SUMMARY OF THE INVENTION

A wear cap including a flexible barrel and a rigid disc enables a high-frequency ultrasonic transducer to properly align to the surface of a material to be tested. The wear cap may be employed for any type of contact sensor that requires a protective wear cap and that needs to align to the surface of a material to be tested. An ultrasonic transducer assembly includes a wear cap and an ultrasonic transducer. The ultrasonic transducer is mounted in the wear cap and includes a transducer body with a cylindrical shape. The flexible barrel has an inner diameter equal to or smaller than an outer diameter of the transducer body such that the flexible barrel stretches to receive the ultrasonic transducer.

A method of producing a wear cap for an ultrasonic transducer includes selecting a flexible material, forming a flexible barrel from the flexible material, selecting a rigid material, forming a rigid disc from the rigid material, and affixing the rigid disc to an end of the flexible barrel. The flexible barrel has a cylindrical shape with an inner diameter equal to or smaller than an outer diameter of the ultrasonic transducer such that the flexible barrel stretches to receive the ultrasonic transducer. The rigid material allows passage of an ultrasonic beam from the ultrasonic transducer.

DETAILED DESCRIPTION OF THE INVENTION

Figure 1:
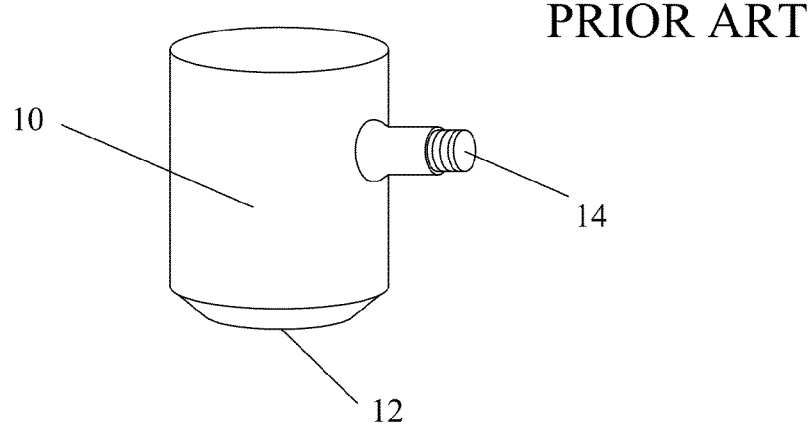
FIG. 1 shows a schematic view of a prior art ultrasonic transducer.
Figure 2:
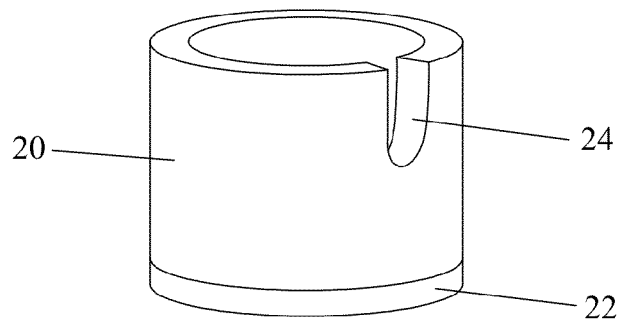
FIG. 2 shows a schematic view of a prior art wear cap for an ultrasonic transducer.
Figure 3:
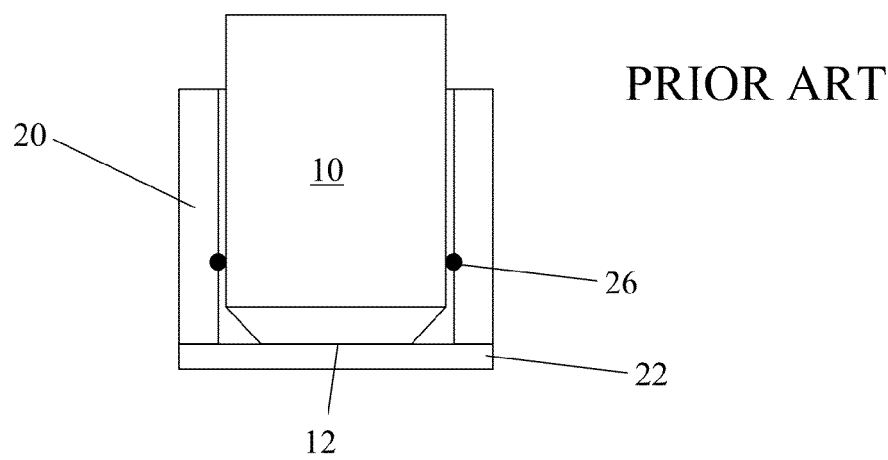
FIG. 3 shows a schematic cross sectional view of the ultrasonic transducer of FIG. 1 mounted in the wear cap of FIG. 2.
Figure 4:
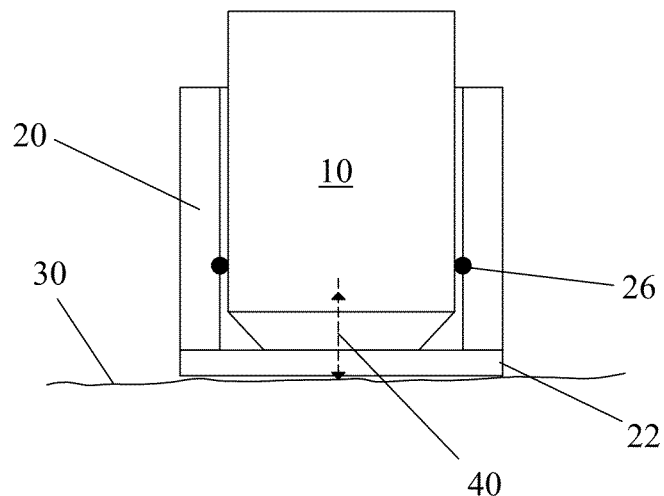
FIG. 4 shows the path of the ultrasonic beam when the ultrasonic transducer of FIG. 1 is properly mounted in the wear cap of FIG. 2.

A protective wear cap with a flexible barrel protects the front face of a high-frequency ultrasonic transducer while simultaneously maintaining good physical contact between the transducer face and the cap material. This wear cap offers utility in many ultrasonic transducer applications, including, but not limited to, high-frequency contact ultrasonic transducers used in pulse/echo layer thickness (PELT) gauges. PELT gauges require that the ultrasonic transducer and protective cap make good contact with a coated test surface such that the PELT gauge is able to make measurements of the coating thicknesses.

The wear cap protects and aligns the face of an ultrasonic transducer to the surface of a material to be tested while enabling and facilitating the passage of an ultrasonic beam between the transducer and the material being tested.

Ultrasonic pulse-echo testing of materials requires an ultrasonic transducer to introduce an ultrasonic stimulus wave into a test material and detect and analyze the reflected ultrasonic waves. The ultrasonic stimulus waves may be either compression or shear waves. It is common for a single ultrasonic transducer to be used both to introduce the stimulus wave and to detect reflected waves.

When a general-purpose contact ultrasonic transducer with a flat front surface is combined with a wear cap, it is then placed against a test material surface, and a measurement is then made. To enable reliable and repeatable high-frequency ultrasonic measurements, it is important that the transducer align to the test surface reliably, even when the transducer and wear cap assembly is placed by an unskilled operator or by a robotic system.

Accordingly, a wear cap apparatus of the present invention preferably facilitates alignment between the transducer and the test material surface so that echoes reflected from the test material are reflected back to the transducer.

In some embodiments, the wear cap apparatus provides protection for the ultrasonic transducer against physical damage.

In some embodiments, the wear cap apparatus is simple to construct, low in cost to manufacture, and small in diameter.

In some embodiments, the wear cap apparatus attaches easily to an ultrasonic transducer and retains its attached position without the need for additional mechanical mechanisms.

In some embodiments, the wear cap apparatus is easily placed on a transducer while allowing trapped air or excess acoustic couplant fluid to be expressed.

In some embodiments, the wear cap apparatus functions properly without the need for a large amount of force to be applied between the transducer and test material.

In some embodiments, the wear cap apparatus holds a small quantity of acoustic coupling fluid.

In some embodiments, the wear cap apparatus is easily replaced when worn or damaged.

In some embodiments, the wear cap apparatus provides a good surface for a user to grip.

In some embodiments, the wear cap apparatus optimizes the amplitude of reflections or echoes produced by a test material.

In some embodiments, the wear cap apparatus eliminates the overlap of test material echoes and artifact echoes.

In some embodiments, the wear cap apparatus prevents the obscuring of test material echoes by other echoes.

In some embodiments, the wear cap apparatus works on both flat and gently curved test material surfaces.

In some embodiments, the wear cap material that lies between the transducer and the test material is an acoustic coupling fluid.

In some embodiments, the wear cap apparatus facilitates the focusing of an ultrasonic beam onto the test material surface.

Figure 5:
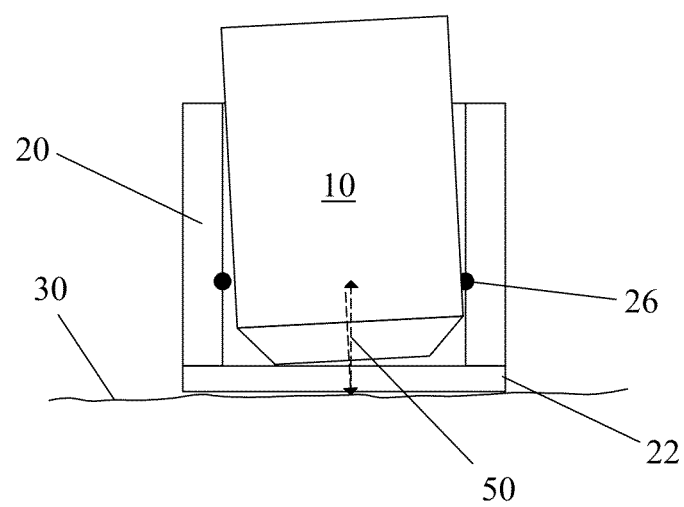
FIG. 5 shows the path of the ultrasonic beam when the ultrasonic transducer of FIG. 1 is improperly mounted in the wear cap of FIG. 2.

Wear caps with rigid barrels and rigid discs have been offered for use with high-frequency PELT transducers. When a rigid protective wear cap is used to cover the active front surface of a high-frequency PELT transducer, it becomes very difficult in many situations to make accurate thickness measurements of coating layers. The insertion of a wear cap between the transducer and the test material surface often interferes with the natural alignment of the transducer to the test material so that ultrasound does not retro-reflect from the coating layers back to the transducer thereby preventing the echoes reflected by the coating layers from being properly detected by the transducer. In addition, the transducer may not make intimate contact with the inside of the wear cap as shown in FIG. 5, and consequently, the ultrasonic waveform quality is reduced due to the wear cap interrupting the passage of ultrasound to the test material.

Many PELT transducers have a flat front surface that is intended to make contact with a test material. When pressed against a relatively flat surface having coating layers, a PELT transducer has a natural tendency to align itself with the surface such that echoes reflected by coating layers end up returning to the transducer. This is caused by the fact that two flat surfaces tend to align when pressed together, and the ultrasound emitted perpendicularly out of the front surface of a transducer reflects back as echoes from the surfaces and returns to the transducer. Adding a rigid wear cap to the front surface of a PELT transducer can interfere with the conduction of ultrasound from the transducer to the coated surface and thus make it difficult to obtain good ultrasonic waveforms. As an example of how misalignment may occur, for high frequency applications, it is necessary for the rigid wear cap to hold a small amount of ultrasonic coupling fluid that facilitates the passage of high-frequency ultrasound from the transducer into the wear cap. This fluid is retained by a 'seal' that is typically in the form of an o-ring between the transducer body and wear cap barrel. Standard mechanical manufacturing tolerances on the wear cap barrel may cause the o-ring to exert a torque on the transducer such that the transducer's front surface cannot make intimate physical contact with the inside surface of the wear cap as shown in FIG. 5. This may cause a user to have to manually apply a large degree of force to the transducer in order to squeeze the transducer, wear cap, and coating surface into good contact with each other. Such misalignment may make it difficult for a user to attain good measurements and may result in undue stress on a user's hand.

A wear cap for high-frequency ultrasonic measurement applications preferably protects the transducer while simultaneously promoting good physical contact and alignment between the transducer front surface and the inside surface of the wear cap. The wear cap design preferably also promotes good contact between the outside surface of the wear cap and the coated surface. To reduce physical stress on the user, this preferably does not require the application of significant force by the user.

Although the wear cap design is described primarily for PELT measurement equipment, the basic structure of the wear cap may satisfy the measurement needs of the ultrasonic industry at large as well as the needs of other measurement technology that employ other types of transducers.

A wear cap design for PELT high-frequency ultrasonic transducers preferably satisfies one or more of the following criteria:

1. The wear cap is simple in design and low-cost to manufacture, and does not require any tight manufacturing tolerances. Rigid wear caps have tight mechanical tolerances and are often costly and difficult to manufacture.

2. The wear cap is small in diameter. The barrel is preferably thin such that the outer diameter of the wear cap-transducer assembly is not much larger than the diameter of the transducer, so it makes good physical contact with gently curved surfaces and is able to fit into the tight confines where the transducer would normally fit. This is a characteristic that conventional rigid wear caps do not possess.

3. The wear cap attaches easily to an ultrasonic transducer and retains its attached position without the need for additional mechanical mechanisms such as retaining clips. This is a characteristic that conventional rigid wear caps sometimes do not possess.

4. The wear cap is easily placed on a transducer while allowing trapped air or excess acoustic couplant to be expressed. Once placed on a transducer, the wear cap then seals against the ingress of contaminants, including, but not limited to, water, dust, and dirt.

5. The wear cap promotes good contact between the wear cap inside surface and the front face of the transducer and also promotes good contact between the outside surface of the wear cap and the coated test surface. In addition, the wear cap promotes good alignment between the ultrasonic transducer and the coated test surface so as to enable coating layer echoes to be detected. This contact and alignment occurs when only a small amount of force is manually applied by the user to press the transducer and wear cap against the surface. To enable this, the wear cap allows some degree of mechanical freedom to the transducer rather than holding it in a fixed alignment as rigid wear caps tend to do. This is a characteristic that conventional rigid wear caps do not possess.

6. The wear cap holds a small reservoir of ultrasonic couplant, which is a fluid designed to eliminate air and to allow the passage of ultrasound between two surfaces, between the front active face of the transducer and the inside surface of the wear cap.

7. The wear cap requires minimal maintenance in that the wear cap is easily and simply replaced when damaged or worn.

8. The wear cap forms a shock-absorbing jacket around the transducer so as to protect the transducer against physical damage.

9. The wear cap provides a comfortable outer surface for a user's hand and is easy to grip. This is a characteristic that conventional rigid wear caps do not possess.

Figure 6A:
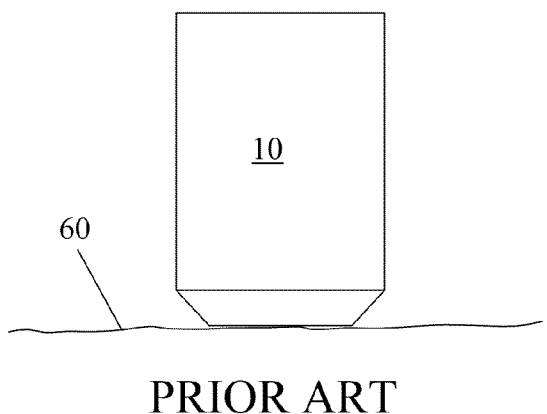
FIG. 6A shows a schematic cross sectional view of a prior art ultrasonic transducer with no protection in contact with a test surface.
Figure 6B:
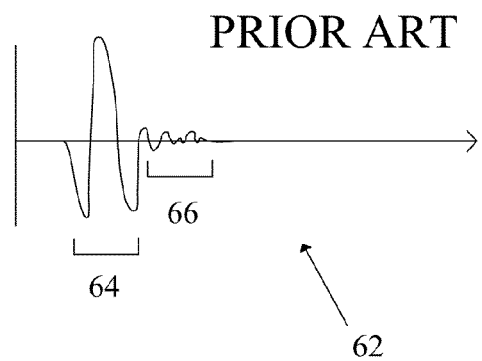
FIG. 6B shows a measurement from the ultrasonic transducer of FIG. 6A.

When ultrasound is emitted by the high-frequency transducer and passes from the front surface of the transducer 10, as shown in FIG. 6A, into some other dissimilar material, such as a paint layer residing on a test material 60, the ultrasonic signal 62 (FIG. 6B) returned to the transducer includes a 'first' echo 64 with a large magnitude generated due to the difference in the acoustic impedance of the transducer and the material. The large 'first' echo can obscure subsequent coating echoes 66 from the test material which are typically much smaller in amplitude, making coating thickness measurements difficult to perform.

Figure 7A:
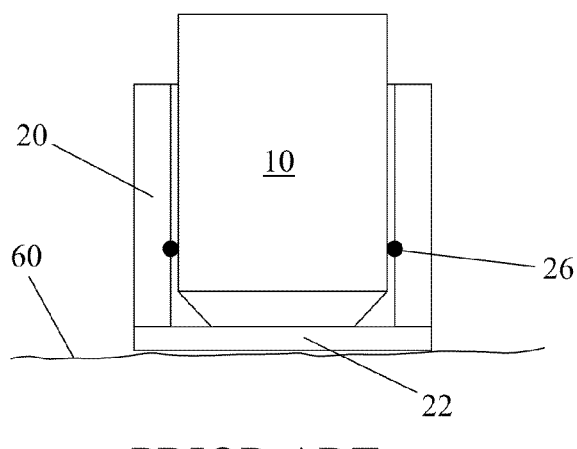
FIG. 7A shows a schematic cross sectional view of a prior art ultrasonic transducer with a wear cap in contact with a test surface.
Figure 7B:
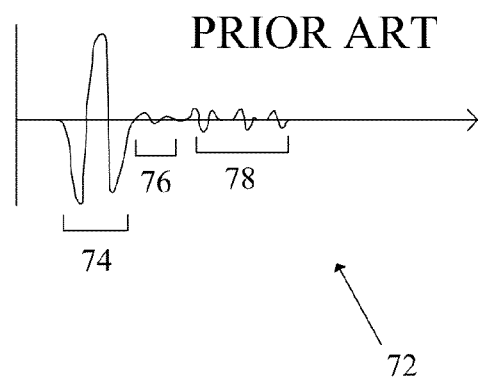
FIG. 7B shows a measurement from the ultrasonic transducer of FIG. 7A.

When a wear cap is positioned between the high-frequency transducer and the test material, careful selection of the wear cap material and thickness alleviates the problem of the large 'first' echo obscuring subsequent echoes. In FIG. 7A, a plastic wear cap is shown which has a rigid disc 22 whose acoustic impedance is similar to the acoustic impedance of coating layers on the test material 60. The ultrasonic signal 72 (FIG. 7B) returned to the transducer includes a 'first' echo 74 generated by the transducer to wear cap interface with a large magnitude due to the difference in the acoustic impedance of the transducer and the material. However, as the ultrasound passes from the wear cap into the coating layers of similar acoustic impedance on the test surface 60, the echoes 78 are typically of similar amplitude. In addition, the wear cap material thickness is chosen to provide good temporal separation 76 between the large first echo 74 and the smaller subsequent echoes 78 from coatings. The first echo 74 thus becomes non-interfering with the coating layer echoes 78, which enables measurements to be made. As such, it can be seen that careful selection of the wear cap material thickness and acoustic impedance improves the performance of the PELT gauge.

The thickness of the rigid disc for a wear cap is preferably selected based on the nature of the measurement being made. When a test material is 'pinged' with ultrasound by a transducer, the ultrasound from the transducer is sent through the wear cap and into the test material. The first echo that returns to the transducer is from the wear cap to test material interface. The next echoes to be returned are from within the test material. The first echo, however, produces a decaying sequence of echoes because that 'ping' bounces back and forth between the front and back surfaces of the wear cap. If the wear cap material is thin enough, the second echo in that decaying sequence may arrive and overlap the echoes being returned by the test material. Hence, the wear cap material is preferably made thick enough to ensure that the second echo does not arrive until after the arrival of echoes from the test material.

The wear cap rigid disc material is preferably carefully selected such that the ultrasonic signal is minimally attenuated. This is important when using high-frequency ultrasound. Although the wear cap rigid disc material and thickness are important, there are a broad range of materials that may be used for the rigid disc, both in terms of material types and in the thickness of the selected material. There is no single preferred material type for all ultrasonic transducer applications, because the best material for the wear cap varies, depending upon the item being measured. Any material may be used for a rigid disc as long as the material passes ultrasound. The material preferably has an acoustic impedance similar to the acoustic impedance of the materials being measured.

For the measurement of paint layers using PELT gauges, since paints have an acoustic impedance similar to plastic due to somewhat plastic-like physical properties, plastics are preferably used for PELT gauge wear cap rigid discs. Preferred plastics for the rigid disc include, but are not limited to, polyesters, polyetherimides, polycarbonates, polyethylenes, polymethylmethacrylates (PMMAs), polyamides, and polytetrafluoroethylenes (PTFEs). Any rigid solid plastic material may be considered for use in a wear cap rigid disc for a PELT gauge for measurement of paint thicknesses on test surfaces. Depending on the specific application, any suitable plastic, resin, or phenolic material may be used to make a wear cap material when measuring paint layers.

As an extension of the above, when measuring test materials whose acoustic impedance is significantly different from that of plastic, an optimal rigid disc material may not be plastic and may instead be a metal, glass, or ceramic material.

Placement of a high-frequency PELT transducer against a coated surface may be accomplished either by hand or by a robotic system. It is thus possible for an unprotected transducer to be damaged by rough surfaces or improper placement against a surface. A wear cap serves to protect the costly high-frequency contact transducer from physical damage resulting from contact with surfaces.

A wear cap is part of a 'sandwich'. This sandwich includes the transducer, the wear cap material, and the surface coatings to be measured. Along the path of the ultrasonic beam, any air must be eliminated in order to propagate ultrasound. Air is eliminated through the use of a coupling fluid on both sides of the wear cap which enables ultrasound to pass from the transducer into the wear cap and from the wear cap into the coating layers. At the same time, the wear cap preferably provides mechanical freedom for the transducer/wear cap and wear cap/coated surface to make good contact and to align properly such that all air is displaced by the coupling fluid and such that the reflected ultrasonic echoes are returned to the transducer. For echoes to be returned to the transducer, the transducer needs to align perpendicularly to the coated surface such that the emitted ultrasonic beam is perpendicular to the surface and thus retro-reflects back to the transducer. When a wear cap is fabricated from rigid materials, it is difficult in some situations to attain the desired alignment, which is one of the problems experienced with the use of rigid wear caps.

Figure 8:
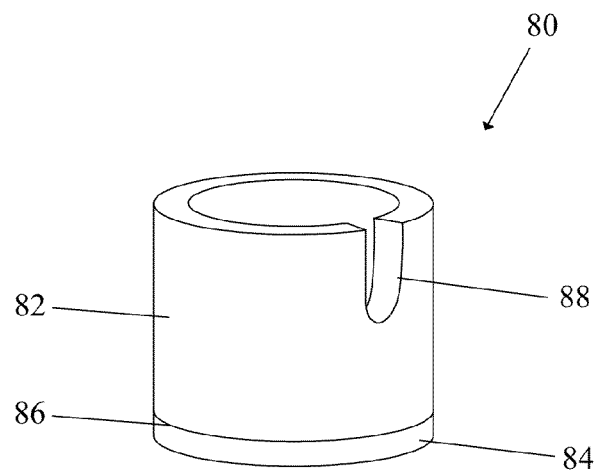
FIG. 8 shows a schematic view of a wear cap in an embodiment of the present invention.

As shown in FIG. 8, in some embodiments of the present invention, the objectives and other advantages are achieved by affixing an end 86 of a flexible and compliant cylindrical barrel 82 to a disc of rigid material 84, thereby forming a wear cap 80 that possesses a cup shape. In this embodiment, since the cylindrical barrel 82 extends above the electrical connector of the ultrasonic transducer, a notch 88 is formed in the wear cap 80 to receive the electrical connector. In other embodiments, the cylindrical barrel 82 is shorter than the electrical connector and does not include a notch 88. This wear cap differs from the conventional wear cap of FIG. 1 in at least several ways. The barrel is made of a flexible material rather than a rigid material. The inner diameter of the flexible barrel is equal to or smaller than the outer diameter of the ultrasonic transducer body, rather than being larger, as in the case of conventional rigid barrel wear caps. The transducer is mounted and maintained in the flexible barrel without the use of an o-ring.

Although the specific material for the flexible barrel of the wear cap is important, there are a broad range of elastomeric materials that may be used for the flexible barrel in embodiments described herein. Materials for use in the wear cap flexible barrel include, but are not limited to, natural rubber, silicone rubber, flexible plastics, and synthetic rubbers, including, but not limited to, styrene-butadiene rubber, polybutadiene rubber, nitryl rubber, ethylene-propylene rubber, butyl rubber, polychloroprene rubber, and latex rubber.

Figure 9:
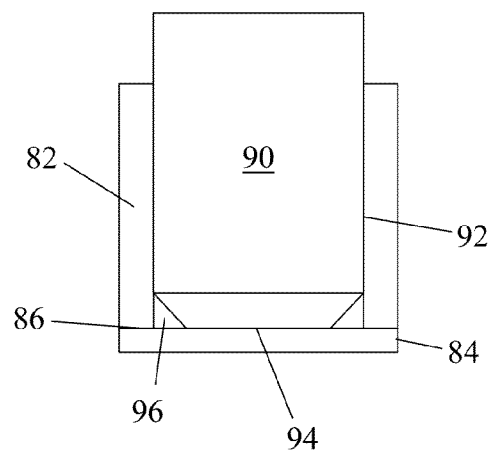
FIG. 9 shows a schematic cross sectional view of an ultrasonic transducer mounted in a wear cap in an embodiment of the present invention.

As shown in FIG. 9, the inner diameter of the wear cap barrel 82 is preferably selected to be sufficiently small in relation to the outside diameter of an ultrasonic transducer 90 such that the wear cap barrel 82 stretches when the transducer 90 is inserted to perform multiple functions, including, but not limited to, gripping the ultrasonic transducer thereby forming a seal 92 against the ingress of dirt or contaminants, holding a small portion of ultrasonic couplant fluid in a reservoir 96 that facilitates the passage of ultrasound across any gap 94 between the transducer 90 and the wear cap disc 84, gripping the transducer 90 to retain the wear cap 80 in its position on the transducer 90, expanding to allow trapped air or excess acoustic couplant to be expressed as the wear cap 80 is placed onto the transducer 90, and flexing to allow the wear cap front surface 84 to align with the transducer front surface and with the test material surface when gentle pressure is applied between the transducer 90 and a test material. The ultrasonic transducer preferably mounts in the wear cap without the use of any o-ring to form a seal between the wear cap and the ultrasonic transducer.

Figure 10:
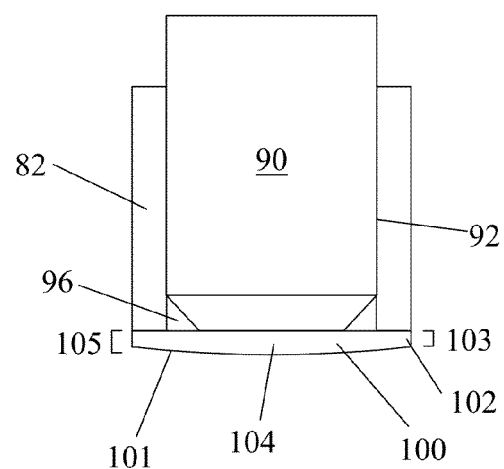
FIG. 10 shows a schematic cross sectional view of an ultrasonic transducer mounted in a wear cap with a curved face in an embodiment of the present invention.

Most high-frequency transducers have small-diameter ultrasonic beams whose diameter is a small fraction of the diameter of the transducer body. Thus, as an extension to the basic wear cap embodiment described herein, an alternative design employs a wear cap material with a non-uniform thickness as shown in FIG. 10. In some embodiments, the wear cap disc 100 possesses a maximum thickness 105 in the center portion 104 through which the ultrasonic beam passes but a reduced thickness 103 at its perimeter 102. The bottom surface 101 preferably has a convex shape to achieve this feature. This allows the wear cap center 104 to make good contact with both the transducer and the coated surface even when the coated surface is mildly curved. The reduced wear cap thickness 103 provides relief for the surface curvature while maintaining good contact between the transducer, wear cap, and coated surface.

Figure 11:
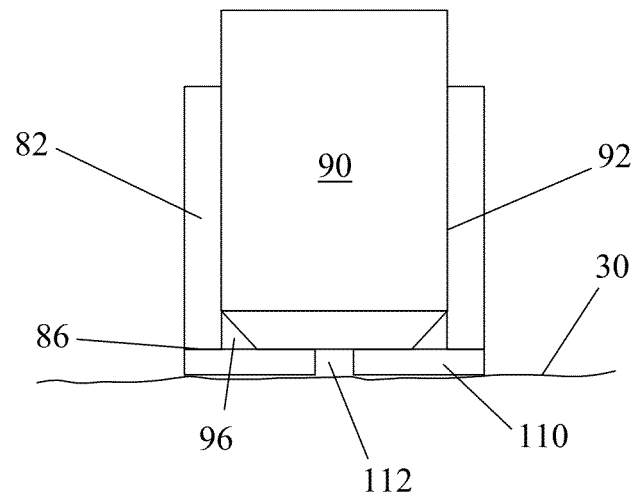
FIG. 11 shows a schematic cross sectional view of an ultrasonic transducer mounted in a fluid-coupled wear cap in an embodiment of the present invention.

As an extension to using a solid material for fabricating a wear cap, it is also possible to propagate ultrasound through a layer of ultrasonic coupling fluid, such as water. As shown in FIG. 11, to create a wear cap that provides the desired advantages while propagating ultrasound only through fluid, the solid wear cap includes a through-opening 112 bored through the wear cap material 110 so that no solid wear cap material remains in the path of the ultrasound. In other words, the wear cap contains an integral opening 112 through which the ultrasonic beam passes and coupling fluid may be injected to fill this opening such that the space between the transducer's front surface and the coated surface is filled with coupling fluid. Any space between the front of the transducer 90 and the coated surface 30 is preferably filled by coupling fluid. In many cases, water is used as the coupling fluid. Water has some desirable characteristics relative to the propagation of ultrasound, and water natively has the ability to eliminate any air gaps that form adjacent to surfaces. As such, the use of water or some other fluid ensures that high-frequency ultrasound is conducted to the surface being tested.

The wear cap preferably retains a coupling fluid that facilitates the conduction of high-frequency ultrasound from the transducer into the wear cap material. Without such a coupling fluid, the ultrasound may be 100% reflected by a thin layer of air trapped between the transducer face and the wear cap. The wear cap thus preferably provides a reservoir 96 for the fluid.

Conventional PELT gauge products employ unfocused contact transducers for the measurement of coating thicknesses, because unfocused transducers provide thickness values that are averages of the coating thicknesses over the entire diameter of the ultrasonic beam. In contrast, in one embodiment herein, a PELT gauge employs a focused transducer. Such a gauge is advantageously able to obtain pinpoint or near-pinpoint thickness measurements rather than the average thickness measurements obtained by a conventional unfocused transducer. In this embodiment, the wear cap material properties are chosen to promote focusing of the ultrasonic beam at the surface of the coating layers of interest.

Figure 12:
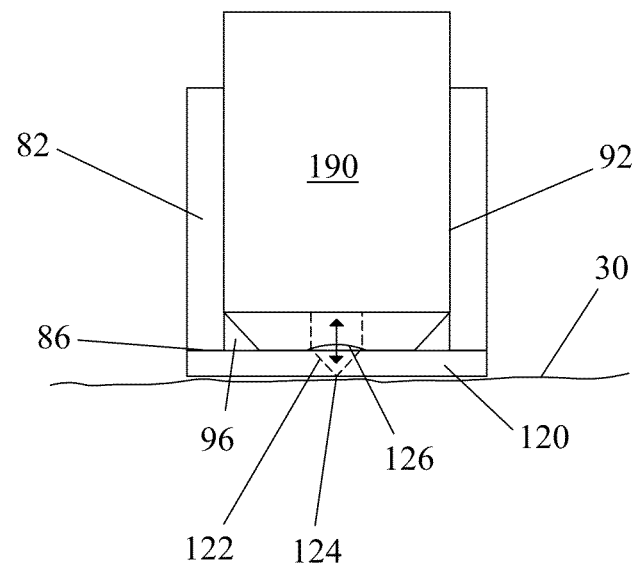
FIG. 12 shows a schematic cross sectional view of a focusing ultrasonic transducer mounted in a wear cap in an embodiment of the present invention.

FIG. 12 shows a wear cap that promotes focusing of the ultrasonic beam along a path 122 toward a single point 124 on the bottom surface of the wear cap disc 120. In this embodiment, the focusing is primarily a feature of the ultrasonic transducer. In other words, there is a concave lens 126 ground into the front surface of the transducer. The lens 126 on the front of the transducer 190 focuses the ultrasound at a particular distance along the path 122 of the ultrasound in 'front' of the transducer 190, a distance that is defined by the lens curvature and the acoustic impedance of the material in front of the transducer. In this embodiment, the beam focuses to the point 124 on the test surface 30, then 'expands' as it reflects such that it approximately follows the same conical beam line back to the transducer as it followed when emitted from the focused transducer. Thus, to ensure that the ultrasound is focused properly on the material to be measured, the wear cap preferably accomplishes two things. First, it retains an acoustic-coupling fluid in the lens cavity of the transducer so that ultrasound passes through the lens and into the wear cap, and second, the wear cap thickness is chosen such that the ultrasound focuses at the surface of the material being tested. If the thickness is too thick or too thin, the focusing is at some other (incorrect) point rather than at the surface of the material being tested. In this embodiment, the echo returns to the transducer 190 to provide a thickness value for a much smaller area of the test surface 30.

Although certain wear cap design features are shown with certain transducer designs in the figures, any of the disclosed wear cap design features may be used in combination with each other and may be used with any of the disclosed apparatus designs.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. An ultrasonic transducer assembly comprising:
   a wear cap comprising:
      a flexible barrel having a cylindrical shape; and
      a rigid disc affixed to an end of the flexible barrel; and
   an ultrasonic transducer mounted in the wear cap with the rigid disc contacting a front face of the ultrasonic transducer, the ultrasonic transducer comprising a transducer body having a cylindrical shape;

wherein the flexible barrel has an inner diameter less than an outer diameter of the transducer body such that the flexible barrel stretches to receive the ultrasonic transducer.

2. The assembly of claim 1, wherein the rigid disc has a thickness tapering from the center to the edges of the disc.

3. The assembly of claim 1, wherein a through-hole through the center of the rigid disc is sized and located such that an ultrasonic beam from the ultrasonic transducer passes through the through-hole rather than passing through the material of the rigid disc.

4. The assembly of claim 1, wherein a thickness of the rigid disc is selected to locate a focus point of an ultrasonic beam of the ultrasonic transducer to coincide with a test surface.

5. The assembly of claim 1 further comprising a coupling fluid displacing any air between the wear cap and the ultrasonic transducer.

6. The assembly of claim 1, wherein the rigid disc is formed to have a thickness such that ultrasonic echoes returned to the ultrasonic transducer from the rigid disc of ultrasound generated by the ultrasonic transducer do not interfere with ultrasonic echoes from a test surface and the rigid disc is formed of a material selected to have an acoustic impedance similar to an acoustic impedance of a test surface or a coating on the test surface.

7. The assembly of claim 1, wherein the rigid disc is made of a material selected from the group consisting of a polyester, a polyetherimide, a polycarbonate, a polyethylene, a polymethylmethacrylate, a polyamide, a polytetrafluoroethylene, a plastic, a resin, and a phenolic material.

8. The assembly of claim 1, wherein the flexible barrel is formed such that a seal is formed between the flexible barrel and the transducer body without using an o-ring.

9. The assembly of claim 1, wherein the flexible barrel is made of a material selected from the group consisting of natural rubber, silicone rubber, flexible plastic, synthetic rubber, styrene-butadiene rubber, polybutadiene rubber, nitryl rubber, ethylene-propylene rubber, butyl rubber, polychloroprene rubber, and latex rubber.

10. A wear cap for an ultrasonic transducer comprising:
a flexible barrel having a cylindrical shape; and
a rigid disc affixed to an end of the flexible barrel;
wherein the flexible barrel has an inner diameter less than an outer diameter of a transducer body of the ultrasonic transducer having a cylindrical shape such that the flexible barrel stretches to receive the ultrasonic transducer and the rigid disc contacts a front face of the ultrasonic transducer.

11. The wear cap of claim 10, wherein the rigid disc has a thickness tapering from the center to the edges of the disc.

12. The wear cap of claim 10, wherein a through-hole through the center of the rigid disc is sized and located such that an ultrasonic beam from the ultrasonic transducer passes through the through-hole instead of passing through the material of the rigid disc.

13. The wear cap of claim 10, wherein a thickness of the rigid disc is selected to locate a focus point of an ultrasonic beam of the ultrasonic transducer to coincide with a test surface.

14. The wear cap of claim 10, wherein the rigid disc is formed to have a thickness such that ultrasonic echoes from the rigid disc do not interfere with ultrasonic echoes from a test surface and the rigid disc is formed of a material having an acoustic impedance similar to an acoustic impedance of a test surface or a coating on the test surface.

15. The wear cap of claim 10, wherein the rigid disc is made of a material selected from the group consisting of a polyester, a polyetherimide, a polycarbonate, a polyethylene, a polymethylmethacrylate, a polyamide, a polytetrafluoroethylene, a plastic, a resin, and a phenolic material.

16. The wear cap of claim 10, wherein the flexible barrel is formed such that a seal is formed between the flexible barrel and the transducer body without using an o-ring.

17. The wear cap of claim 10, wherein the flexible barrel is made of a material selected from the group consisting natural rubber, silicone rubber, flexible plastic, synthetic rubber, styrene-butadiene rubber, polybutadiene rubber, nitryl rubber, ethylene-propylene rubber, butyl rubber, polychloroprene rubber, and latex rubber.

18. A method of producing a wear cap for an ultrasonic transducer, the method comprising the steps of:
a) selecting a flexible material;
b) forming a flexible barrel from the flexible material having a cylindrical shape with an inner diameter less than an outer diameter of the ultrasonic transducer such that the flexible barrel stretches to receive the ultrasonic transducer and the rigid disc contacts a front face of the ultrasonic transducer;
c) selecting a rigid material allowing passage of an ultrasonic beam from the ultrasonic transducer;
d) forming a rigid disc from the rigid material; and
e) affixing the rigid disc to an end of the flexible barrel, wherein the wear cap comprises the flexible barrel and the rigid disc affixed to the end of the flexible barrel.

19. The method of claim 18, wherein the rigid disc is formed to have a thickness such that ultrasonic echoes returned to the ultrasonic transducer from the rigid disc of ultrasound generated by the ultrasonic transducer do not interfere with ultrasonic echoes from a test surface and the rigid disc is formed of a material selected to have an acoustic impedance similar to an acoustic impedance of a test surface or a coating on the test surface.

* * * * *

UNITED STATES PATENT AND TRADEMARK OFFICE
CERTIFICATE OF CORRECTION

PATENT NO. : 8,841,823 B2  
APPLICATION NO. : 13/242025  
DATED : September 23, 2014  
INVENTOR(S) : Todd Jackson Page 1 of 1

It is certified that error appears in the above-identified patent and that said Letters Patent is hereby corrected as shown below:

In the Claims,

Claim 17 (Column 12, lines 23-24): replace "the group consisting natural rubber" with "the group consisting of natural rubber"

Signed and Sealed this
Sixteenth Day of December, 2014

Michelle K. Lee
*Deputy Director of the United States Patent and Trademark Office*